United States Patent [19]

Okamoto

[11] Patent Number: 4,994,565

[45] Date of Patent: Feb. 19, 1991

[54] NUCLEOTIDE SEQUENCE OF GENE SPECIFICALLY EXPRESSED BY INSULINOMA

[75] Inventor: Hiroshi Okamoto, Sendai, Japan

[73] Assignee: Tohoku University, Sendai, Japan

[21] Appl. No.: 87,803

[22] Filed: Aug. 21, 1987

[30] Foreign Application Priority Data

Aug. 22, 1986 [JP] Japan .................................. 61-195168

[51] Int. Cl.$^5$ ...................... C07H 15/12; C07H 19/06; C12Q 1/68; G01N 33/566
[52] U.S. Cl. .......................................... 536/27; 435/6; 436/501; 536/26
[58] Field of Search .............. 435/6; 436/501; 536/26, 536/27

[56] References Cited

PUBLICATIONS

Chemical Abstracts, vol. 89, No. 13, 9-25-78, p. 283, Abstract #102160q, J. R. Duguid et al: "Identification of the Major Polyadenylated Transcription Products and the Genes Active in Their Synthesis in a Rat Insulinoma," Proc. Natl Acad Sci U.S.A., 1978, 75(7), 3249-53.

Chemical Abstracts, vol. 89, No. 9, 8-28-78, p. 162, Abstract #72225n, M. A. Permutt et al: "Cell-Free Translation of Messenger RNA Extracted from a Human Insulinoma," J. Clin. Endocrinol. Metab. 1978, 46(6).

Chemical Abstracts, vol. 106, No. 3, 1-19-87, p. 178, Abstract #13898f, Columbus, Ohio, U.S. F. S. Takasawa et al: "Novel Gene Activated in Rat Insulinomas," Diabetes, 1986, 35(10), 1178-80.

Primary Examiner—Amelia Burgess Yarbrough
Assistant Examiner—Mindy B. Fleisher
Attorney, Agent, or Firm—Fleit, Jacobson, Cohn, Price, Holman & Stern

[57] ABSTRACT

From a cDNA library, a nucleotide sequence of a novel gene, called rig, specifically expressed by streptozotocin- or alloxan-nicotinamide-induced rat insulinomas was determined. Further, novel genes with base sequences homologous to rig were found in a BK virus-induced hamster insulinoma and in a surgically removed human insulinoma. The above DNA is transcribed to provide an mRNA. The above DNAs and mRNAs can be efficaciously employed for the medical purposes of pancreatic diseases.

5 Claims, 4 Drawing Sheets

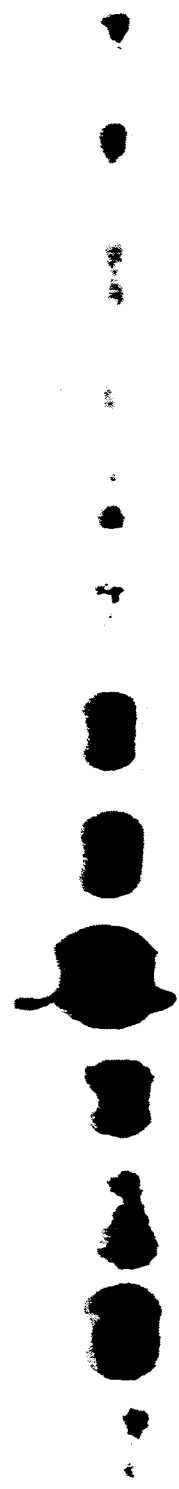
FIG_1

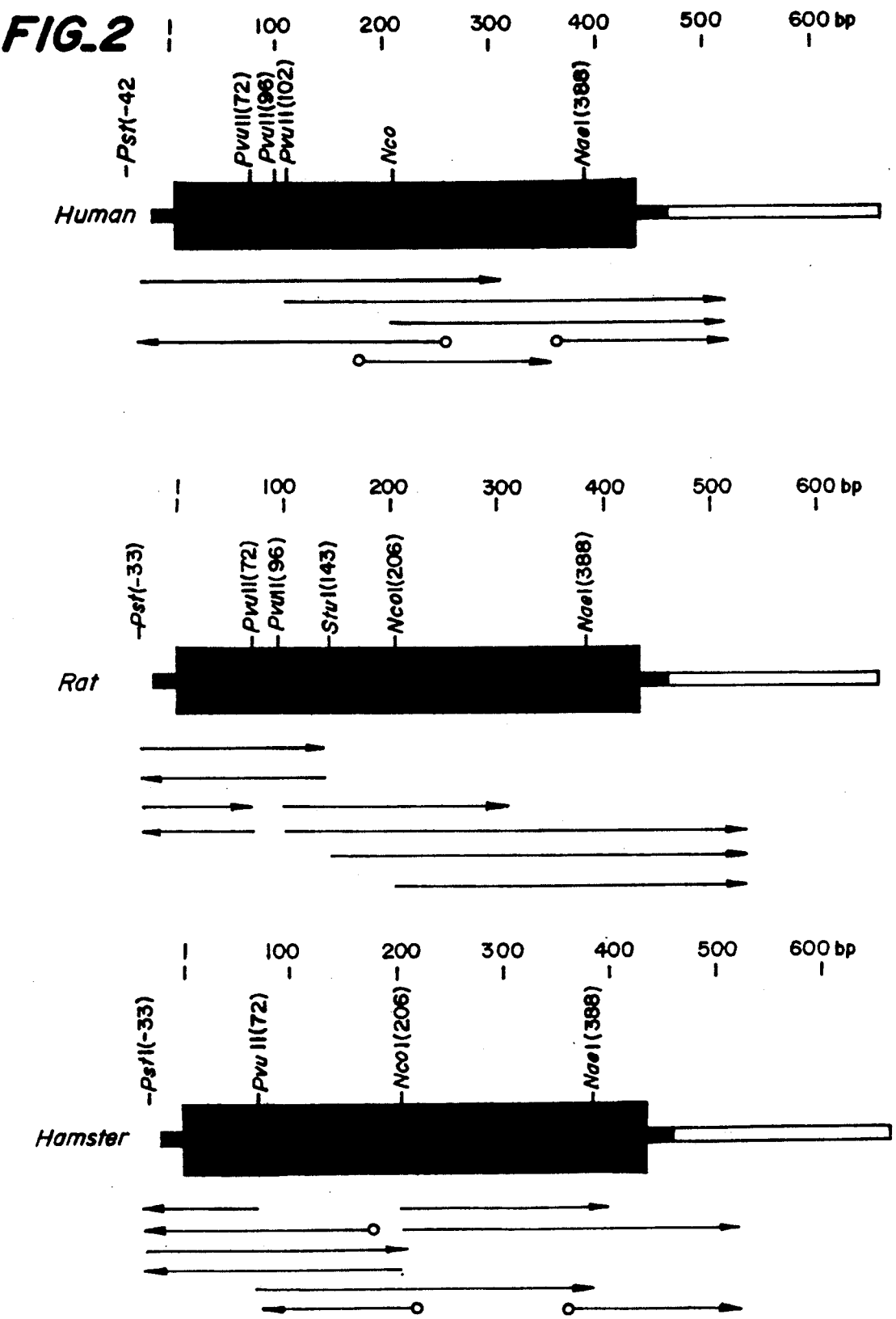

```
                    90                    95                   100                   105
Human   Pro Glu Met Val Gly Ser Met Val Gly Val Tyr Asn Gly Val Tyr Lys Thr Phe Asn Gln Val Glu Ile Lys Pro
        CCC GAG ATG GTG GGC AGC ATG GTC GGT GTG TAC AAC GGC GTG TAC AAG ACC TTC AAC CAG GTG GAG ATC AAG CCC
Rat     Pro Glu Met Val Gly Ser Met Val Gly Val Tyr Asn Gly Val Tyr Lys Thr Phe Asn Gln Val Glu Ile Lys Pro
        CCC GAG ATG GTC GGC AGC ATG GTG GGT GTG TAC AAC GGC GTG TAC AAG ACC TTC AAC CAG GTG GAG ATC AAA CCC
Hamster Pro Glu Met Val Gly Ser Met Val Gly Val Tyr Asn Gly Val Tyr Lys Thr Phe Asn Gln Val Glu Ile Lys Pro
        CCC GAG ATG GTG GGC AGC ATG GTG GGC GTG TAC AAC GGC GTG TAC AAG ACC TTC AAC CAG GTG GAG ATC AAG CCT 110                   115                   120                   125                   130
Human   Glu Met Ile Gly His Tyr Leu Gly Glu Phe Ser Ile Thr Tyr Lys Pro Val Lys His Gly Arg Pro Gly
        GAG ATG ATC GGC CAC TAC CTG GGC GAG TTC TCC ATC ACC TAC AAG CCC GTA AAG CAT GGC CGG CCC GGC
Rat     Glu Met Ile Gly His Tyr Leu Gly Glu Phe Ser Ile Thr Tyr Lys Pro Val Lys His Gly Arg Pro Gly
        GAG ATG ATC GGC CAC TAC CTG GGC GAG TTC TCC ATC ACC TAC AAG CCT GTG AAG CAC GGC CGG CCC GGC
Hamster Glu Met Ile Gly His Tyr Leu Gly Glu Phe Ser Ile Thr Tyr Lys Pro Val Lys His Gly Arg Pro Gly
        GAG ATG ATC GGC CAC TAC CTG GGC GAG TTC TCC ATC ACC TAC AAG CCG GTG AAG CAC GGC CGG CCC GGC 135                   140                   145
Human   Ile Gly Ala Thr His Ser Ser Arg Phe Ile Pro Leu Lys End
        ATC GGG GCC ACC CAC TCC TCC ATC CCT CTC AAG TAA CTCAGCTAATAAAGGGCCACATGACTCCAn
Rat     Ile Gly Ala Thr His Ser Ser Arg Phe Ile Pro Leu Lys End
        ATT GGT GCC ACC CAC TCC TCC CGA TTT ATC CCC AAG TAG TGGGGACACAATAAAGACTCGTTTCAGCCAn
Hamster Ile Gly Ala Thr His Ser Ser Arg Phe Ile Pro Leu Lys End
        ATC GGT GCT ACC CAC TCC TCC CGG TTC ATC CCG CTC AAG TAA CTGCCCAATAAAGACTCTAGAGTGCCAn
```

NUCLEOTIDE SEQUENCE OF GENE SPECIFICALLY EXPRESSED BY INSULINOMA

BACKGROUND OF THE INVENTION

1. Field of the Invention

The present invention relates to a novel gene, more particularly, a novel gene specifically expressed in rat, hamster and human insulinomas, respectively, and to a protein encoded by the gene.

2. Description of the Prior Art

Heretofore, there have not been found nucleotide sequences of genes specifically expressed by human and other animals' insulinomas, and accordingly, products of the genes, i.e., encoded proteins, also have not been known. Further, mechanisms of production, tumorigenic (insulinoma) transformation, regeneration and proliferation, of insulin generating cells have not been elucidated, and so it is the existing state that a diagnosis for finding out the tumorigenic transformation of insulin generating cells also has not yet been developed.

SUMMARY OF THE INVENTION

As a result of an extensive research conducted to elucidate the mechanism to control the insulin biosynthesis and to develop a simplified diagnosis for insulinomas, the inventor has determined, from a complementary DNA (cDNA) library, the entire base sequence (487 bases) of a novel gene specifically expressed by streptozotocin-nicotinamide-induced or alloxan-nicotinamide-induced rat insulinomas, and designated it as rig (rat insulinoma gene). Further, the inventor has succeeded to deduce the entire amino acid sequence (145 amino acids) of a protein encoded by the novel gene.

The present invention was accomplished based on the above findings.

BRIEF DESCRIPTION OF THE DRAWINGS

For better understanding of the invention, reference is taken to the accompanying drawings.

FIG. 1 is an autoradiograph by Northern blot of mRNA whose level is increased in rat insulinomas. Namely, 25 μg of RNA are electrophoresed on 1.5% (wt./vol.) agarose gel and transferred onto a nitrocellulose filter. Lane 1 shows an RNA from the islets of Langerhans; lanes 2~4, RNAs from insulinomas induced by the combined administration of streptozotocin and nicotinamide; lanes 5~7, RNAs from insulinomas induced by the combined administration of alloxan and nicotinamide; lane 8, an RNA from regenerating islets of Langerhans; lanes 9~11, RNAs from liver, kidney and brain of untreated rats, respectively; and lanes 12 and 13, RNAs from livers of tumorbearing rats treated with streptozotocin and nicotinamide and with alloxan and nicotinamide, respectively. Arrows indicate 28S, 18S and 4S RNAs run on the gel.

FIG. 2 shows a sequence determination for nucleic acid of genes specifically expressed by rat, hamster and human insulinomas, respectively. Nucleotide numbers are given on the right. Numbers of the nucleotide immediately 5' to the restriction site are indicated in parentheses. The heavy line indicates an open reading frame. The open box indicates poly(A) tract. Arrows show the origin, direction and extent of the sequence determination.

FIG. 3A and FIG. 3B show nucleotide and deduced amino acid sequences of cloned cDNAs corresponding to mRNAs whose level has been specifically increased in rat, hamster and human insulinomas, respectively. Though the respective sequences are serial, they have been divided into FIG. 3A and FIG. 3B for convenience sake. Nucleotide residues are numbered in the 5' to 3' direction, beginning with the first residue of ATG triplet encoding the initiator methionine. The deduced amino acid sequence is given above the nucleotide sequences, and amino acid residues are numbered beginning with the initiator methionine. The polyadenylation signal (AATAAA) is underlined, and comparing with the above nucleotide sequence of rig cDNA, different portions in the nucleotide sequences of the hamster and human cDNAs are marked with an asterisk.

DETAILED DESCRIPTION OF THE INVENTION

The present invention will be explained in more detail hereinafter.

As is seen from FIG. 1, since scarcely any rig was expressed in the normal pancreatic islets of Langerhans or regenerating and proliferating B-cells of islets of Langerhans, it is considered to be possible that rig is intimately involved in the oncogenic proliferation of B-cells. As a result of a further study, novel genes with nucleotide sequences homologous to rig have been found in a BK virus-induced hamster insulinoma and in a surgically removed human insulinoma. Namely, the nucleotide sequences of the respective novel genes isolated from cDNA libraries of hamster insulinomas and of human insulinomas are 90% or more identical and the deduced amino acid sequences encoded thereby are 100% identical with rig isolated from rat insulinomas. The protein deduced from this amino acid sequence has a molecular weight of 17,040, contains no signal peptide, is abundant of basic amino acids, and has a structure similar to a nuclear location signal.

The background of the study for the present invention will be described hereinafter.

Alloxan and streptozotocin have been known as an experimental diabetogenic agent and recently found to break and fragmentize, in a very short period of time, the DNA of the islets of Langerhans. The breaks by alloxan of DNA are considered to be effected by an active oxygen, i.e., a hydroxyl radical (OH.), while the DNA breaking action of streptozotocin is considered to be caused by an alkylation of DNA. In eukaryotic cells, when DNA is damaged, a poly-adenosine diphosphate (poly ADP) ribose synthetase existing in the nuclear chromatin is considered to become activated to repair the damage. The poly(ADP-ribose) synthetase in the cell nuclei of the islets of Langerhans is considerably activated in a serial course substantially similar to the DNA breaking. Nicotinamide adenine dinucleotide (NAD), a substrate of this enzyme, is almost depleted in the islets of Langerhans, resulting in a considerable decrease of the pro-insulin synthesis.

On the other hand, as a mechanism of B-cell oncogenesis of the islets of Langerhans, it is considered that, in the above-mentioned course of mechanism, when the enzyme activity is controlled by a poly(ADP-ribose) synthetase inhibitor, such as nicotinamide, the amount of NAD is maintained, preventing the decrease of the pro-insulin synthesis, but the repair of the DNA breaks is retarded. Such a retardation of the repair of the DNA breaks is considered to increase the possibility of gene structure alteration, inducing structure alterations in oncogenes as well as some growth stimulator genes, which may result in the B-cell oncogenesis.

In the case where insulin-dependent diabetes is induced by the B-cell DNA damage, since B-cells are the terminally differentiated cells which hardly divide and proliferate, the pro-insulin synthesis is considered to reduce, due to NAD depletion by a suicidal response to repair the DNA damages, rather than due to the DNA damages themselves bringing about fatal results directly upon the life of B-cells. On the other hand, the poly-(ADP-ribose) synthetase inhibitors hinder the suicidal response and maintain the B-cell NAD level, saving the B-cells from the necrosis and, however, there may be a possibility of a B-cell oncogenesis from an abnormality of the DNA repair. Namely, it is conjectured that a response to repair DNA, i.e., the genetic code, to the normal state even at the sacrifice of cell function may be the direction of the development of insulin-dependent diabetes, while the B-cells would survive, maintaining their cellular functions as they are and leaving some abnormalities of the gene (DNA) repair, may be the direction of the generation of insulinomas.

Figure 3A:
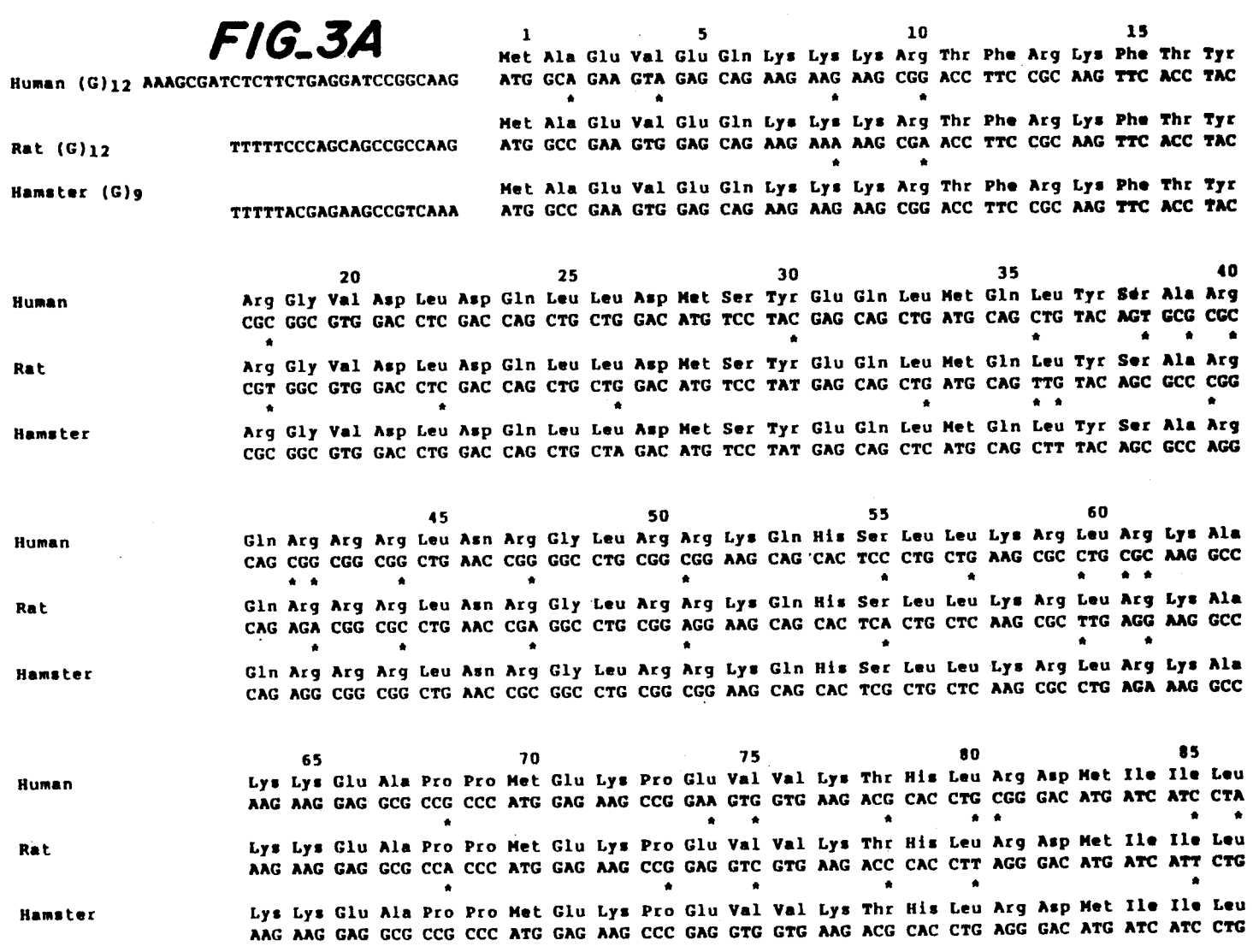

According to the present invention, a novel protein having an amino acid sequence described in FIGS. 3A and 3B is provided.

Further, according to the present invention, a DNA which has the nucleotide sequence encoding the amino acid sequence of the above-mentioned novel protein is provided.

As the above nucleotide sequence, mention may be made of the nucleotide sequence shown in FIGS. 3A and 3B of genes specifically expressed by human insulinomas, rat insulinomas and hamster insulinomas, respectively.

Furthermore, according to the present invention, the above DNA is transcribed to provide an mRNA.

These novel proteins, DNAs having the abovementioned nucleotide sequence, and the above mRNAs can be very efficaciously employed for the purpose of medicine for pancreatic diseases, such as a diagnosis of insulinomas or pancreas cancers.

The embodiments of the present invention will be explained in more detail by way of examples hereinafter which are not intended as limitations thereof.

EXAMPLE 1

(a) Preparation of mRNA

Using arbitrarily bred male Wistar rats weighing 150-200 g, insulinomas were induced by the combined administration of streptozotocin-nicotinamide or alloxan-nicotinamide, and the islets of Langerhans were isolated by the collagenase-digestion method described in Mol Cell. Biochem. 37, 43-61 (1981). Regenerating islets were prepared by the method of Yonemura et al. described in Diabetes 33, 401-404 (1984). From these islets of Langerhans, respective RNAs were extracted according to the method of Chirgwin et al. described in Biochemistry 18, 5294-5299 (1979). From these RNAs, poly(A)+RNAs were isolated by the oligo(dT)-cellulose column chromatography according to the method of Aviv and Leder described in Proc. Natl. Acad. Sci. USA 69, 1408-1412 (1972).

(b) Preparation of cDNA Library

With 2 μg of poly(A)+RNA from streptozotocin-nicotinamide-induced insulinomas as a template, a cDNA was prepared according to the method of Okayama and Berg described in Mol. Cell. Biol. 2, 161-170 (1982). Then, this cDNA was used to transform DH1, a strain of *Escherichia coli* K12, according to the method of Yamamoto et al. described in J. Biol. Chem. 261, 6156-6159 (1986), and a cDNA library of 170,000 transformants was constructed. Further, using a BK virus-induced hamster insulinoma and a surgically removed human insulinoma, other cDNA libraries were constructed in the same manner.

(c) Northern Blot Hybridization

Twenty five μg of RNA obtained in the foregoing paragraph (a) were electrophoresed on a 1.5% (wt./vol.) agarose gel containing 1.1 M formaldehyde and transferred onto a nitrocellulose filter according to the method of Ohsawa et al. described in Biochem. Biophys. Res. Commun. 132, 885-891 (1985). Then, after subjecting to heat-treatment at 80° C. for 2 hours, this filter was hybridized to $^{32}$P-Pst I-Nae I DNA fragment obtained in Example 3 illustrated hereinafter and autoradiographed (refer to FIG. 1).

(d) Nucleotide Sequencing

DNA sequence was determined by the dideoxy-chain termination method of Messing described in Methods Enzymol. 101, 20-78 (1983). Namely, cloned cDNAs corresponding to mRNAs increased in rat insulinomas which were cleaved with restriction endonucleases and M13 phage DNAs cleaved with restriction endonucleases were treated with $T_4$ DNA ligase to combine cDNA with a vector, whereby recombinant phage double-stranded DNAs were prepared. Then, a transfection (DNA transfection) was performed by adding ligated DNAs to calcium chloride-treated host bacteria, followed by cultivation on an X-gal (5-bromo-4-chloro-3-indoryl-β-D-galactoside) solution-containing agar plate, and infected bacteria were selected. The thus obtained infected bacteriophage was proliferated and treated with polyethylene glycol, whereby a recombinant phage single-stranded DNA was prepared. In order to effect an annealing, using this recombinant phage single-stranded DNA as a template, a primer complementary to the phage DNA region adjacent to the cloning position was heated at 55° C. for 5 minutes and then left standing at 37° C. for 30 minutes. Next, the annealed reactant solution was admixed with [α-$^{32}$]dCTP and DNA polymerase I Klenow fragment, and put dividingly into 4 tubes. Four kinds of deoxynucleotides respectively with 1 kind of 2',3'-dideoxynucleotide were mixed into the respective tubes and a complementary DNA chain extending reaction was carried out. The DNA chain extension stopped at the position where 2',3'-dideoxynucleotide was taken in. Then, after this complementary chain had stopped, the solution was applied on a polyacrylamide gel (6% or 8%), electrophoresed and subsequently autoradiographed to translate the base sequence, whereby the cloned cDNA base sequence corresponding to mRNA increased in rat insulinomas was determined.

Example 2

The Pst I-Nae I DNA fragment obtained in Example 3 described below was hybridized to the RNA obtained in the above-described Example 1(a) (0.7 kilobase). As shown in FIG. 1, the RNA was clearly present at a much higher level in each insulinoma induced by streptozotocin and nicotinamide (lanes 2-4) than in normal islets of Langerhans (lane 1). Similarly, the level of the 0.7 kilobase RNA was also increased in the alloxan-nicotinamide-induced insulinomas (lanes 5-7). On the other hand, the level of the 0.7 kilobase RNA was low in regenerating islets of Langerhans (lane 8) as well as in untreated rat livers (lane 9), kidneys (lane 10) and brains (lane 11), in streptozotocinnicotinamide combinedly administered tumor-bearing rat livers (lane 12) and alloxan-nicotinamide combinedly administered tumor-bearing rat livers (lane 13). Further, though the data is not shown, the level of the 0.7 kilobase RNA was increased in the BK virus-induced hamster insulinoma and the surgically removed human insulinoma, while the level of the 0.7 kilobase RNA was low in human tumors such as scirrhous carcinoma of stomach, pulmonary carcinoma, and papillary carcinoma of thyroid.

EXAMPLE

From the cDNA library of 170,000 transformants obtained in Example 1(b), about 5,000 clones were duplicated on nitrocellulose filters for differential screening. One set of filters was hybridized to =P-cDNA that was reverse transcribed from poly(A)+ RNA of insulinomas with oligo(dT) as a primer and =P-dCTP. The other set of filters was hybridized to =P-cDNA that was prepared, in the same manner as the case of the above insulinomas, from poly(A)+ RNA of normal islets of Langerhans. In the differential screening of 5,000 clones, 1 clone consistently was hybridized specifically to =P-cDNA from insulinomas. Plasmid DNA was isolated from the above specific clone and cleaved with Pst I and Nae I. As shown in FIG. 2, the 421 base-pair (430 base-pair for human) Pst I -Nae I DNA fragment was labeled by nick translation with =P-dCTP and utilized to probe for levels of the corresponding mRNA species in rat insulinomas.

EXAMPLE 4

The nucleotide sequence was determined of the cloned cDNA corresponding to the mRNA whose level was increased in rat insulinomas. As shown in FIGS. 3A and 3B, the cDNA stretched 487 (498 and 485 for human and hamster, respectively) nucleotides plus poly(A) and had one large open reading frame, coding for a protein of 145 amino acids (molecular weight, 17,040) on the assumption that ATG at nucleotides 1-3 is the start codon and TAG at nucleotides 436-438 is the stop codon. The nucleotide sequence of CCAAGATGG around the methionine codon agreed well with the initiation sequence characteristic of many eukaryotic mRNAs. The protein deduced from the nucleotide sequence was a highly basic protein (31 residues of arginine plus lysine vs. 14 residues of glutamic acid plus aspartic acid) with a putative nuclear location signal at amino acid residues 61-68. There were no clusters of hydrophobic amino acid residues characteristic of a signal peptide. These results indicate that the protein may interact with intranuclear acidic macromolecules such as DNA. The weak hybridization signal in normal islets of Langerhans could be attributed to either the lower level of mRNA in the normal cells (FIG. 1, lane 1) or the structural difference n the mRNA between tumor and normal cells.

From a rat pancreatic islet cDNA library prepared according to the method of Yamamoto et al. described in J. Biol. Chem. 261, 6156-14 6159 (1986), a normal cDNA was isolated and its nucleotide sequence was determined. This sequence was found to be identical to that of insulinomas. This fact indicated that the difference in band intensity observed in the Northern blot hybridization (FIG. 1) was solely due to the difference in the amounts of the mRNA in tumor and normal cells. The nucleotide and deduced amino acid sequences of the cDNA characterized as the above were screened for relationships to other genes and proteins stored in the nucleic acid and protein data banks of the European Molecular Biology Laboratory (Heidelberg), GenBank (Cambridge, Mass.), the National Biomedical Research Foundation (Washing D.C.) with the rapid similarity search algorithm of Wilbur et al. described in Proc. Natl. Acad. Sci. USA, 80, 726-730 (1983). This screen indicated that there were neither genes nor gene products that were identical or highly homologous to the cDNA, although there was only a slight homology (52%) between nucleotide residues 99-174 of the cDNA and the 3' terminal region (nucleotide residues 1070-1145) of the rat c-mos.

As is demonstrated by the above Examples, the novel genes named rig has been found in both strptozotocin-nicotinamide-induced insulinomas and alloxan-nicotinamide-induced insulinomas. Streptozotocin and alloxan differ not only in chemical structure but also in the mode of DNA strand breaks. Examination of insulinomas induced by streptozotocin and by alloxan indicates that the activation of rig may be a general feature of pancreatic B-cell tumorigenic transformation. In fact, rig was activated in hamster insulinomas induced by BK virus according to the method of Yamamoto et al. described in Experientia 36, 187-188 (1980), or in surgically removed human insulinomas. As is clear from FIGS. 3A and 3B, the respective novel genes isolated from cDNA libraries of hamster insulinomas and of human insulinomas were 92% and 91% identical respectively in the nucleotide sequence, and 100% identical in the deduced 145 amino acid sequence encoded thereby, with rig isolated from rat insulinomas. However, there was not seen any specific expression of rig in human tumors such as scirrhous carcinoma of stomach, pulmonary carcinoma and papillary carcinoma of thyroid.

What is claimed is:

1. A DNA comprising one of the following nucleotide sequences:

| | |
|---|---|
| ATGGCAGAAG TAGAGCAGAA GAAGAAGCGG | 30 |
| ACCTTCCGCA AGTTCACCTA CCGCGGCGTG | 60 |
| GACCTCGACC AGCTGCTGGA CATGTCCTAC | 90 |
| GAGCAGCTGA TGCAGCTGTA CAGTGCGCGC | 120 |
| CAGCGGCGGC GGCTGAACCG GGGCCTGCGG | 150 |
| CGGAAGCAGC ACTCCCTGCT GAAGCGCCTG | 180 |
| CGCAAGGCCA AGAAGGAGGC GCCGCCCATG | 210 |
| GAGAAGCCGG AAGTGGTGAA GACGCACCTG | 240 |
| CGGGACATGA TCATCCTACC CGAGATGGTG | 270 |
| GGCAGCATGG TGGGCGTCTA CAACGGCAAG | 300 |
| ACCTTCAACC AGGTGGAGAT CAAGCCCGAG | 330 |
| ATGATCGGCC ACTACCTGGG CGAGTTCTCC | 360 |
| ATCACCTACA AGCCCGTAAA GCATGGCCGG | 390 |
| CCCGGCATCG GGGCCACCCA CTCCTCCCGC | 420 |
| TTCATCCCTC TCAAG | 435 | which is specifically expressed in a human insulinoma;

| | |
|---|---|
| ATGGCCGAAG TGGAGCAGAA GAAAAAGCGA | 30 |
| ACCTTCCGCA AGTTCACCTA CCGTGGCGTG | 60 |
| GACCTCGACC AGCTGCTGGA CATGTCCTAT | 90 |
| GAGCAGCTGA TGCAGTTGTA CAGCGCCCGG | 120 |
| CAGAGACGGC GCCTGAACCG AGGCCTGCGG | 150 |
| AGGAAGCAGC ACTCACTGCT CAAGCGCTTG | 180 |
| AGGAAGGCCA AGAAGGAGGC GCCACCCATG | 210 |
| GAGAAGCCGG AGGTCGTGAA GACCCACCTT | 240 |
| AGGGACATGA TCATTCTGCC CGAGATGGTC | 270 |
| GGCAGCATGG TGGGTGTGTA CAACGGCAAG | 300 |
| ACCTTCAACC AGGTGGAGAT CAAACCCGAG | 330 |
| ATGATCGGCC ACTACCTGGG CGAGTTCTCC | 360 |

| | |
|---|---|
| ATCACCTACA AGCCTGTGAA GCACGGCCGG | 390 |
| CCCGGCATTG GTGCCACCCA CTCCTCCCGA | 420 |
| TTTATCCCCC TCAAG | 435 | which is specifically expressed in rat insulinomas; and

| | |
|---|---|
| ATGGCCGAAG TGGAGCAGAA GAAGAAGCGG | 30 |
| ACCTTCCGCA AGTTCACCTA CCGCGGCGTG | 60 |
| GACCTGGACC AGCTGCTAGA CATGTCCTAT | 90 |
| GAGCAGCTCA TGCAGCTTTA CAGCGCCAGG | 120 |
| CAGAGGCGGC GGCTGAACCG CGGCCTGCGG | 150 |
| CGGAAGCAGC ACTCGCTGCT CAAGCGCCTG | 180 |
| AGAAAGGCCA AGAAGGAGGC GCCGCCCATG | 210 |
| GAGAAGCCCG AGGTGGTGAA GACGCACCTG | 240 |
| AGGGACATGA TCATCCTGCC CGAGATGGTG | 270 |
| GGCAGCATGG TGGGCGTGTA CAACGGCAAG | 300 |
| ACCTTCAACC AGGTGGAGAT CAAGCCTGAG | 330 |
| ATGATCGGCC ACTACCTGGG CGAGTTCTCC | 360 |
| ATCACCTACA AGCCGGTGAA GCACGGCCGG | 390 |
| CCCGGCATCG GTGCTACCCA CTCCTCCCGG | 420 |
| TTCATCCCGC TCAAG | 435 | which is specifically expressed in a hamster insulinoma.

2. The DNA claimed in claim 1, wherein said nucleotide sequence is specifically expressed in a human insulinoma.

3. The DNA claimed in claim 1, wherein said nucleotide sequence is specifically expressed in a rat insulinoma.

4. The DNA claimed in claim 1, wherein said nucleotide sequence is specifically expressed in a hamster insulinoma.

5. An mRNA which is transcribed from the DNA claimed in claim 1.

* * * * *

UNITED STATES PATENT AND TRADEMARK OFFICE
CERTIFICATE OF CORRECTION

PATENT NO. : 4,994,565

DATED : February 19, 1991

INVENTOR(S) : Hiroshi Okamoto

It is certified that error appears in the above-indentified patent and that said Letters Patent is hereby corrected as shown below:

The Drawing Sheet, consisting of Fig. 3B, should be deleted to be replaced with the Drawing Sheet, consisting of Fig. 3B, as shown on the attached page.

Signed and Sealed this

Twenty-sixth Day of July, 1994

Attest:

BRUCE LEHMAN

Attesting Officer     Commissioner of Patents and Trademarks

FIG. 3B

```
                        90                    95                   100                  105
Human        Pro Glu Met Val Gly Ser Met Val Gly Val Tyr Asn Gly Lys Thr Phe Asn Gln Val Glu Ile Lys Pro
             CCC GAG ATG GTG GGC AGC ATG GTG GGC GTC TAC AAC GGC AAG ACC TTC AAC CAG GTG GAG ATC AAG CCC Rat          Pro Glu Met Val Gly Ser Met Val Gly Val Tyr Asn Gly Lys Thr Phe Asn Gln Val Glu Ile Lys Pro
             CCC GAG ATG GTC GGC AGC ATG GTG GGT GTG TAC AAC GGC AAG ACC TTC AAC CAG GTG GAG ATC AAA CCC Hamster      Pro Glu Met Val Gly Ser Met Val Gly Val Tyr Asn Gly Lys Thr Phe Asn Gln Val Glu Ile Lys Pro
             CCC GAG ATG GTG GGC AGC ATG GTG GGC GTG TAC AAC GGC AAG ACC TTC AAC CAG GTG GAG ATC AAG CCT 110                  115                  120                  125                  130
Human        Glu Met Ile Gly His Tyr Leu Gly Glu Phe Ser Ile Thr Tyr Lys Pro Val Lys His Gly Arg Pro Gly
             GAG ATG ATC GGC CAC TAC CTG GGC GAG TTC TCC ATC ACC TAC AAG CCC GTA AAG CAT GGC CGG CCC GGC Rat          Glu Met Ile Gly His Tyr Leu Gly Glu Phe Ser Ile Thr Tyr Lys Pro Val Lys His Gly Arg Pro Gly
             GAG ATG ATC GGC CAC TAC CTG GGC GAG TTC TCC ATC ACC TAC AAG CCT GTG AAG CAC CGG CCC GGC Hamster      Glu Met Ile Gly His Tyr Leu Gly Glu Phe Ser Ile Thr Tyr Lys Pro Val Lys His Gly Arg Pro Gly
             GAG ATG ATC GGC CAC TAC CTG GGC GAG TTC TCC ATC ACC TAC AAG CCG GTG AAG CAC CGC CCC GGC 135                  140                  145
Human        Ile Gly Ala Thr His Ser Ser Arg Phe Ile Pro Leu Lys End
             ATC GGG GCC ACC CAC TCC TCC CGC TTC ATC CCT CTC AAG TAA  TGG CTCAGCTAATAAGGCGCACATGACTCCAn Rat          Ile Gly Ala Thr His Ser Ser Arg Phe Ile Pro Leu Lys End
             ATT GGT GCC ACC CAC TCC CGA TTT ATC CCC CTC AAG TAG  TGGGGACAATAAAGACTCGTTTCAGCCAn Hamster      Ile Gly Ala Thr His Ser Ser Arg Phe Ile Pro Leu Lys End
             ATC GGT GCT ACC CAC TCC CGG TTC ATC CCG CTC AAG TAA  CTGCCCAATAAAGACTCTAGAGTGCCAn
```